United States Patent
Lawrence

(10) Patent No.: US 10,281,318 B1
(45) Date of Patent: May 7, 2019

(54) IN LINE WEB PROCESS MEASUREMENT APPARATUS AND METHOD

(71) Applicant: SolveTech, Inc., Wilmington, DE (US)

(72) Inventor: Douglas Lawrence, Wilmington, DE (US)

(73) Assignee: SolveTech, Inc., Wilmington, DE (US)

(*) Notice: Subject to any disclaimer, the term of this patent is extended or adjusted under 35 U.S.C. 154(b) by 0 days.

(21) Appl. No.: 15/937,142

(22) Filed: Mar. 27, 2018

Related U.S. Application Data

(60) Provisional application No. 62/479,419, filed on Mar. 31, 2017.

(51) Int. Cl.

| | |
|---|---|
| *G01G 17/02* | (2006.01) |
| *G01G 21/28* | (2006.01) |
| *G01B 7/06* | (2006.01) |
| *G01B 15/02* | (2006.01) |
| *G01N 9/24* | (2006.01) |
| *G01N 21/89* | (2006.01) |

(52) U.S. Cl.
CPC .............. *G01G 21/28* (2013.01); *G01B 7/087* (2013.01); *G01G 17/02* (2013.01); *G01N 9/24* (2013.01); *G01B 2210/44* (2013.01); *G01N 21/8901* (2013.01)

(58) Field of Classification Search
CPC ........ G01G 9/005; G01G 17/02; G01G 21/28; G01G 23/35; G01B 7/087; G01B 2210/44; G01N 9/24; G01N 21/8901
See application file for complete search history.

(56) References Cited

U.S. PATENT DOCUMENTS

| | | |
|---|---|---|
| 3,531,827 A | 10/1970 | Dragonette |
| 4,404,634 A | 9/1983 | Bautz |
| (Continued) | | |

FOREIGN PATENT DOCUMENTS

| | | |
|---|---|---|
| CN | 201455009 U | 5/2010 |
| DE | 102013017289 A1 | 4/2015 |
| DE | 202014001175 U1 | 6/2015 |
| GB | 2479572 | 10/2011 |
| WO | 2016198690 | 12/2016 |

OTHER PUBLICATIONS

Capacitance Thickness Gauges; New Designs Break Old Barriers, J. H. Schut (2005).

(Continued)

*Primary Examiner* — Randy W Gibson
(74) *Attorney, Agent, or Firm* — Rogowski Law LLC

(57) ABSTRACT

An apparatus for measuring thickness and/or basis weight of a web or film has a frame defining a measurement channel between two opposing frame faces. A first sensor component is on or appended to the first face and a second sensor component is on or appended to the second face of the frame. A series of rollers guide the web or film into the measurement channel in an overlapping relation such that at least two portions of said web reside in said measurement channel for detection by the sensor. The frame may be a C-frame gauge, and the sensor may be two capacitor plates. One sensor component is a source, while the opposing sensor component is sensitive to the source emission. The combined thickness of the portions of the web residing in the measurement channel is determined based upon the degree to which the web or film attenuates the emission.

19 Claims, 8 Drawing Sheets

(56) References Cited

U.S. PATENT DOCUMENTS

| | | | |
|---|---|---|---|
| 4,542,297 A | | 9/1985 | Hold |
| 4,591,726 A | * | 5/1986 | Schenk .............. G01N 21/8901 250/559.03 |
| 5,569,835 A | | 10/1996 | Kenney |
| 5,735,055 A | | 4/1998 | Hochbein |
| 7,593,106 B2 | * | 9/2009 | Hellstrom .............. G01N 21/57 356/429 |
| 8,982,337 B2 | | 3/2015 | Miller |
| 9,151,595 B1 | | 10/2015 | Cook |
| 9,335,145 B2 | | 5/2016 | Sonntag |
| 9,354,090 B2 | * | 5/2016 | Beselt .................. D21G 9/0009 |
| 9,927,366 B2 | * | 3/2018 | Tixier .................... G01N 21/31 |
| 2007/0280415 A1 | | 12/2007 | Waterson |
| 2015/0226549 A1 | | 8/2015 | Wu |
| 2016/0252343 A1 | | 9/2016 | Fuellmeier |
| 2016/0265901 A1 | | 9/2016 | Kyriakis |
| 2016/0282277 A1 | * | 9/2016 | Tixier ................ G01B 11/0625 |

OTHER PUBLICATIONS

Online Laser Measurement Technology for Rolled Products, R. Noll and M. Krauhausen (Dec. 31, 2008).

C-frame Systems for Thickness Measurement of Flat Film, Micro Epsilon, http://www.micro-epsilon.com/download/products/cat--systems--plastics-processing--en.pdf (2017).

Multichannel TM Array Gauge Thickness Gauging System, Solve Tech, http://gauging.com/multichanneltm-array-gauge/ (2017).

Isiss General Brochure, Isiss, http://www.google.com/ (2017).

Inline Profile Thickness Measurement Systems for Plastics, British Plastics & Rubber, https://dialog.proquest.com/professional/docview/1398597878/15A7BA37EB42AG7B341/44?accountide=157282 (2017).

Web Gauging Solutions, Thermo Fisher Scientific, https://tools.thermofisher.com/content/sfs/brochures/D20372~.pdf (2017).

* cited by examiner

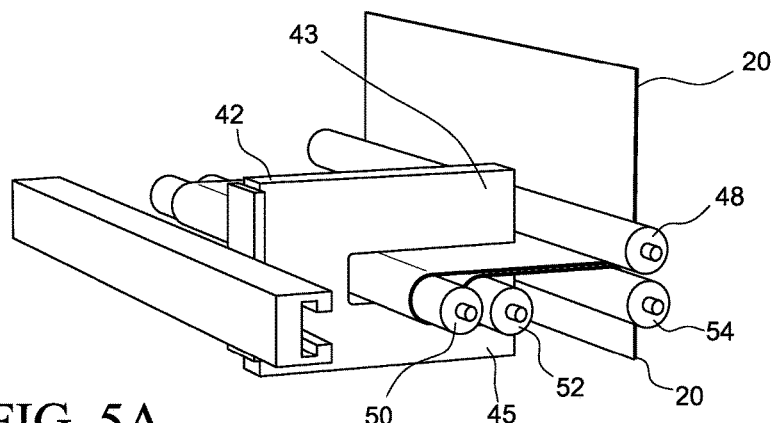
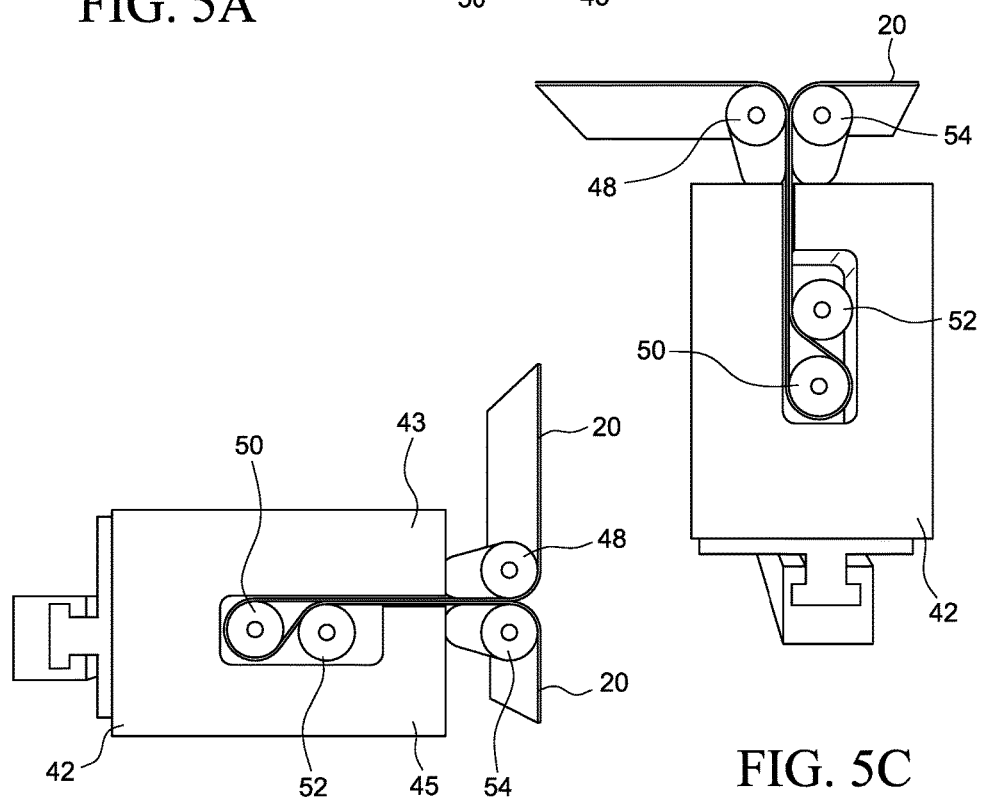
FIG. 5A
FIG. 5B
FIG. 5C

IN LINE WEB PROCESS MEASUREMENT APPARATUS AND METHOD

CROSS-REFERENCE TO RELATED APPLICATION

This application claims priority under 35 USC § 119(e) to U.S. Provisional Application Ser. No. 62/479,419, entitled "In Line Web Process Measurement Apparatus and Method", filed Mar. 31, 2017, the disclosure of which is incorporated by reference herein.

FIELD OF THE INVENTION

The present invention relates to thickness, basis weight, and other gauging apparatus, systems and methods to measure key material properties of a web or film during manufacturing processes.

BACKGROUND

FIG. 1 shows an O-frame thickness measurement gauge sensor scanner 10. O-frame thickness measurement gauge sensor scanners are commonly used to measure the thickness and/or basis weight of metal, plastic, rubber, nonwoven or other web materials 20 produced in sheet or strip form. The web material 20 is passed through the O-frame opening 12 of a defined width 14 and height 16 and between sensors 22, 24 disposed on opposing faces of the frame 12. In many cases, the sensors are non-contact sensors. Drawbacks of O-frame thickness measurement gauge scanners include that the fixed distance and registration of sensor pairs are difficult to achieve and maintain stably. Weaknesses are in part directly linked to inherent registration issues of the independent mounting surfaces provided by the translating elements incorporated in the O-frame. Moreover, as the width of a web widens, there is greater difficulty to maintain registration and distance of supporting structures of the sensor components, which adversely impacts the quality of the measurements. Furthermore, mechanical wear and tear on translating elements can lead to long term degradation of registration, which directly affects the integrity and reliability of the measurement over time.

C-frame scanning gauges with non-contact sensors sometimes are used to measure thickness and/or basis weight of a web material. In many cases, use is limited to measuring along either or both edges of the web owing to drawbacks in large through depth geometries. Once such drawback is best understood by viewing the arms of the C frame construction as a pair of cantilevered beams. As beam length increases, the tips of the beams to which sensor pairs are affixed are subject to ever greater upsets in positional stability, both individually and differentially. A second drawback can be seen by the negative impact of off line excursion requirements. In the off-line position, the rear locus of the C Frame often violates the spatial constraints of a given process envelope as it relates to available aisle space and/or prohibitive impingement on regions directly adjacent to the process apparatus. These off-line excursions are frequently mission critical (a) to avoid mechanical interference of the sensors with the web during string-up operations and/or (b) to provide periodic retraction of the sensors from the running web for dynamic re-standardization purposes.

The industry continues to seek improvements and effective alternatives for apparatus and methods to determine accurate thickness of web and film materials.

BRIEF SUMMARY OF THE INVENTION

In a first aspect, an apparatus for measuring thickness or basis weight of a web or film includes a frame having a first face spaced apart in opposing relation to a second face defining a measurement channel. A sensor comprises a first sensor component that is on or appended to the first face of the frame, and a second sensor component that is on or appended to the second face of the frame. The sensor may be a non-contact displacement sensor, such as parallel plate capacitive sensors, x-ray tube and detector sensors, beta source and beta detector sensors, gamma source and gamma detector sensors, and pulsed terahertz sources and sensors, including reflective plate geometries. For example, if a parallel plate capacitive sensor is used, the first sensor component is the first plate and the second sensor component is the second plate of the parallel plate pair. In one advantageous embodiment, the second sensor plate can be divided into multiple regions that afford a multiplicity of capacitive shapes arranged in an array.

The apparatus further includes a series of rollers adapted for contact with the web or film to guide the web or film into the measurement channel in an overlapping relation such that at least two portions of said web or film reside in said measurement channel for detection by the sensor. While a first embodiment of the invention shows two portions of the web overlapping, the series of rollers can be configured so that more than two portions of said web reside in said measurement channel for detection by the sensor.

A linear slide is present to which the frame is secured. The linear slide is adapted for cross-web movement for scanning the web width in its entirety or to locate the frame along different locations across the web or film. Moreover, the linear slide may be adapted for movement to locate the sensor to a position off of the web or film.

The frame may further define a reference channel spaced apart from the measurement channel, which reference channel registers a same or substantially same spaced apart distance as the measurement channel between the first face and second face of the frame.

Optionally, a second sensor pair may be provided that is integral with or affixed to the frame. Optionally, an adjunct sensor may be provided that is integral with or affixed to the frame. Such adjunct sensors include temperature sensors, moisture sensors, and color sensors.

In a second aspect of the invention, a method for measuring thickness or basis weight of a web or film includes the steps of (1) threading the web or film over a series of rollers to guide the web or film into a measurement channel in an overlapping relation such that at least two portions of said web or film reside in said measurement channel, and (2) detecting attenuation of a signal from a sensor source at one side of the measurement channel to a detector at an opposite side of the measurement channel. The series of rollers may be configured so that more than two portions of said web reside in said measurement channel for detection by the sensor.

In the method according to this embodiment of the invention, a non-contact displacement sensor may be used. Examples of non-contact displacement sensors include: capacitive sensors, x-ray tube and detector sensors, beta source and beta detector sensors, gamma source and gamma detector sensors, and pulsed terahertz sources and sensors, including those that use reflective plate geometries.

A third step of the method may be (3) traversing the measurement channel by cross-web movement to locate the measurement channel along different locations across the web or film. And the fourth step of the method may be (4) traversing the measurement channel by cross-web movement to locate the measurement channel off of the web or film. In such embodiments, the measurement channel is defined in a frame, and the frame further defines a reference channel spaced apart from the measurement channel, wherein gap spacing of the measurement channel is established with reference to gap spacing of the reference channel. For example, the sensor may comprise a capacitive sensor having a first plate located at one side of the measurement channel and a second plate located at an opposite side of the measurement channel. In one advantageous embodiment of the method, the second plate has multiple regions of different capacitance arranged in an array.

DESCRIPTION OF THE DRAWINGS

The foregoing summary, as well as the following detailed description of the disclosure, will be better understood when read in conjunction with the appended drawings. For the purpose of illustrating the disclosure, there is shown in the drawings an embodiment of a double back scanner which is presently preferred. It should be understood, however, that the disclosure is not limited to the precise arrangements and instrumentalities shown. In the drawings:

FIGS. 5A-C are schematic diagrams of the Double-Back Scanner with C-Frame Gauge of FIG. 2 shown in horizontal and vertical orientation;

DETAILED DESCRIPTION OF EMBODIMENTS

Figure 1:
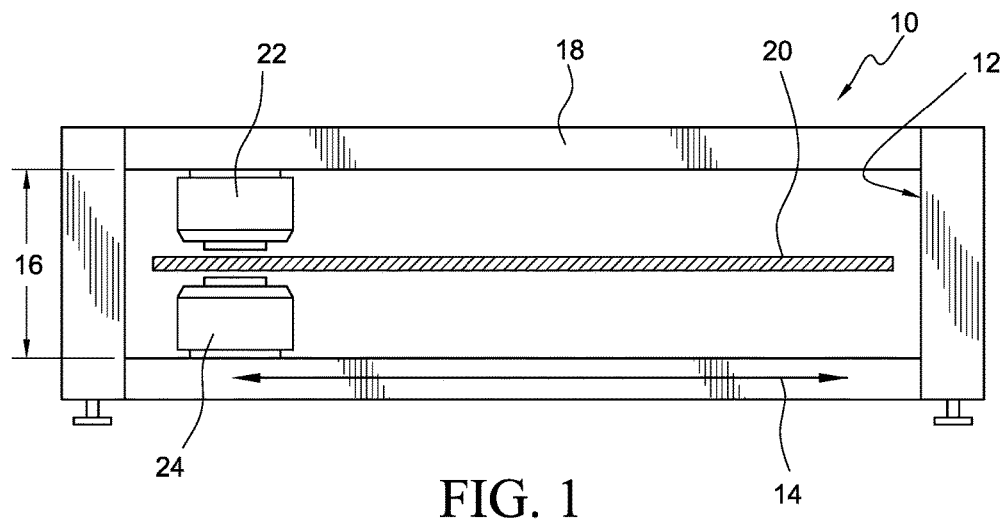
FIG. 1 is a schematic diagram of an O-frame thickness measurement gauge sensor scanner according to the Prior Art.

Certain terminology is used in the following description for convenience only and is not limiting. The words "lower," "bottom," "upper," "top," "right" and "left" designate directions in the drawings to which reference is made. The words "inwardly," "outwardly," "upwardly" and "downwardly" refer to directions toward and away from, respectively, the geometric center of the headrest, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It also should be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 2:
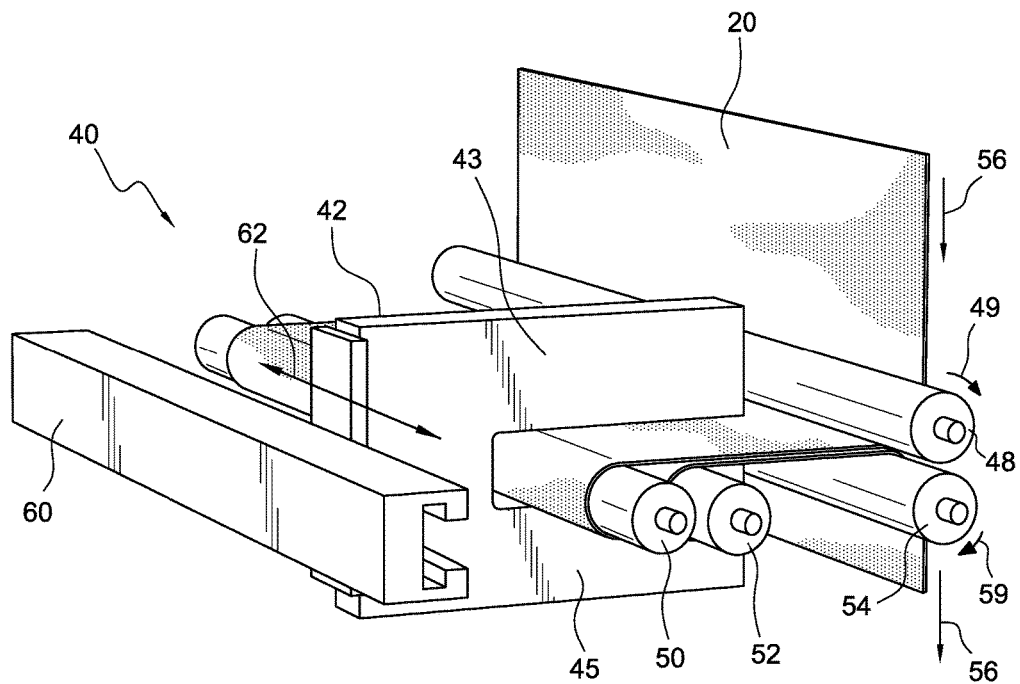
FIG. 2 is a schematic diagram of a perspective view of a Double-Back Scanner with C-Frame Gauge according to one embodiment of the invention.

According to a first embodiment of the invention, a "double back" scanner 40 (shown in FIG. 2) has series of rollers 48, 50, 52, 54 in combination with a C-Frame Scanner 42. This embodiment is referred to as a "double back" scanner, because the rollers 48, 50, 52, 54 are configured to guide the web or film 20 for which thickness is to be measured into a measurement channel 58 (see FIGS. 3 and 4) between the first arm 43 and second arm 45 of the C-Frame scanner 42 in an overlapping or "double layer" configuration. If desired, the rollers 48, 50, 52, 54 alternatively could be configured with additional rollers to guide even more layer thicknesses of the web or film 20 into the measurement channel 58 for detection by the scanner 44, 46. For example, three layer or four layer thicknesses of the web or film could be directed into the measurement channel. The depth of the measurement channel and the number of rollers may be adjusted to accommodate the additional web layer thicknesses.

The web 20 travels in the directions of arrows 56 into the measurement channel 58 from roller 48, about rollers 50 and 52 inside the C-Frame scanner 42, through the measurement channel 58 again, thus presenting two layers of the web 20 in the measurement channel 58 and out of the measurement channel 58 about roller 54. Roller 48 is rotated clockwise in direction of arrow 49, and roller 54 is rotated clockwise in direction of arrow 59 (See FIG. 2). Roller 50 is rotated counterclockwise, and roller 52 is rotated clockwise in the embodiment shown in FIG. 2.

Figure 7A:
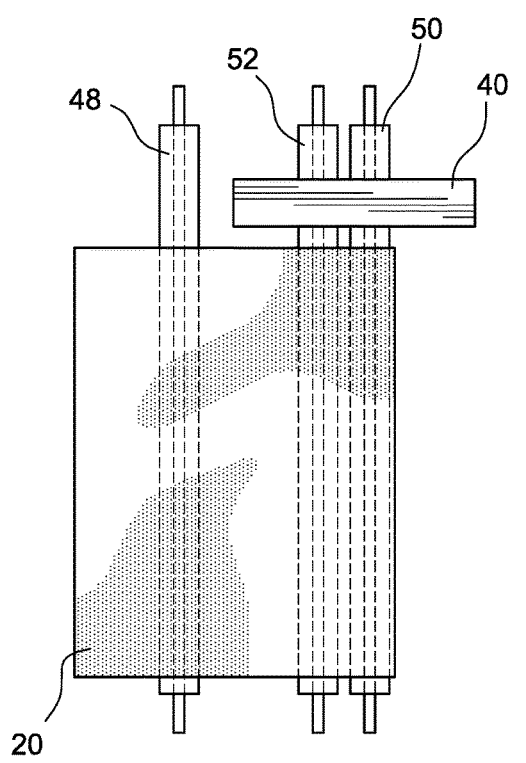
FIGS. 7A and 7B are schematic diagrams illustrating the Double-Back Scanner with C-Frame Gauge of FIG. 2 in an off-web position and in an on-web position for cross-web scanning.
Figure 7B:
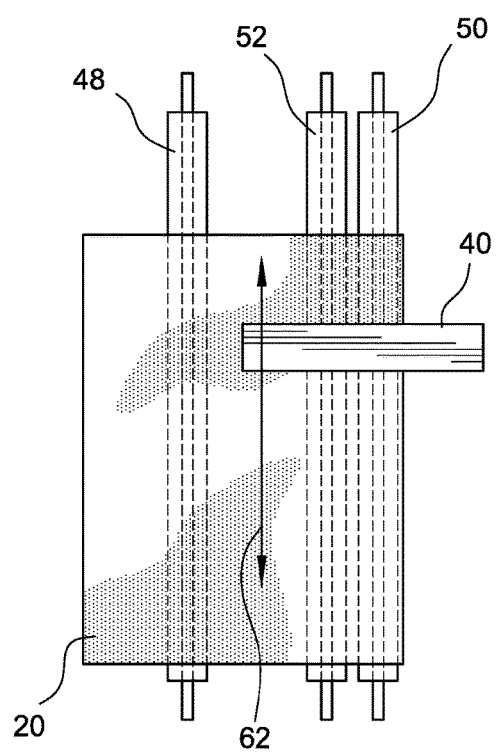

The C-Frame Scanner 42 may be used in conjunction with a linear slide 60 to move the measurement channel 58 across the web 20, such as in the directions of arrow 62. The linear slide 60 also may move the measurement channel 58 off of the web 20 for calibrating. See, e.g., FIGS. 7A and 7B.

The double back scanner 40 including the C-Frame Scanner 42 may be used in any desired orientation, as shown in FIGS. 5A, 5B and 5C. The double back scanner 40 may be disposed in a horizontal orientation as shown in FIGS. 5A and 5B, or alternatively in a vertical orientation as shown in FIG. 5C. In either orientation, the double back scanner accurately measures sensor data without need for sensors to contact the web 20. One half of the sensor provides a source while the opposing half houses a sensor that is sensitive to the source emission. The web 20 acts and an attenuator. Using such sensor data, the average thickness of the web 20 passing through the C-Frame 42 may be calculated.

An upstream sensor (not shown) may be combined with the double back scanner 40 to sense out of limits web thickness and shut down the line or move the linear slide 60 to take the measurement channel 58 off of the web 20 to prevent damage.

The rollers may be of a kind commonly available throughout the web handling industry. They often are made of steel, and have a variety of coatings, including rubber. Rollers are chosen based on physical properties, including diameter, roller bearings, and surface requirements. Roller diameters of 2 inch, 4 inch and 6 inch are commonly in use. In terms of roller diameter, the wider the web, generally a larger diameter roller is required to get necessary rigidity/performance. The scanners according to the invention may accommodate roller selection consistent with other rollers used in a given process. The inner envelope dimensions of the C frame that is associated with the measurement may be modified to accommodate rollers of any desired size. The C frame is mounted to the bracket using fasteners and can incorporate the use of an adapter plate as needed to accommodate differences in mounting geometries, including mounting hole patterns.

Figure 6A:
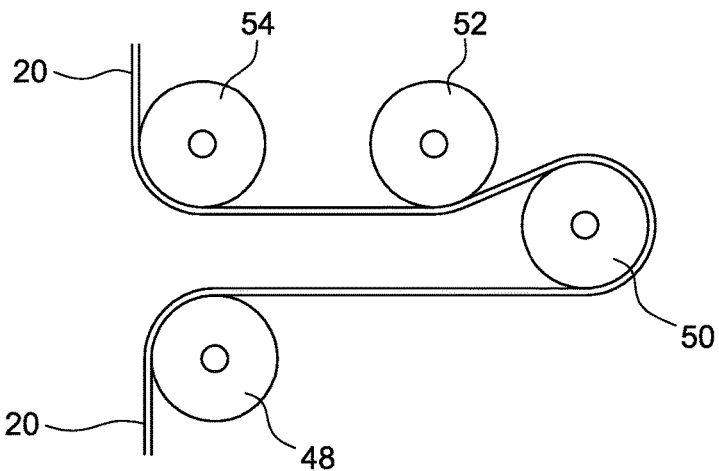
FIGS. 6A-C are schematic diagrams illustrating a method for stringing a web onto the rollers of the Double-Back Scanner with C-Frame Gauge of FIG. 2.
Figure 6B:
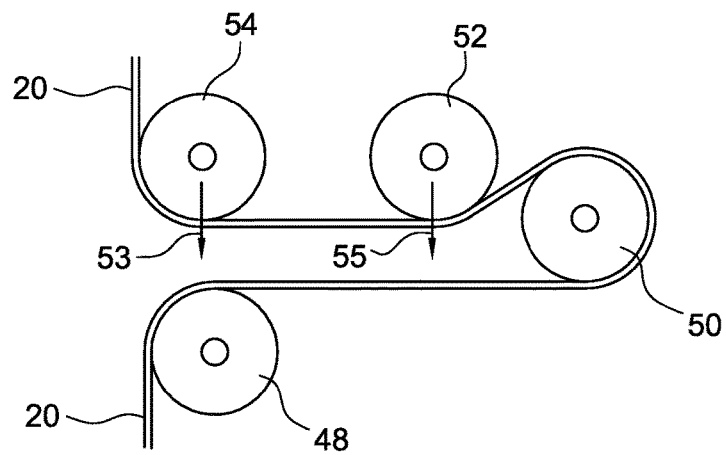
Figure 6C:
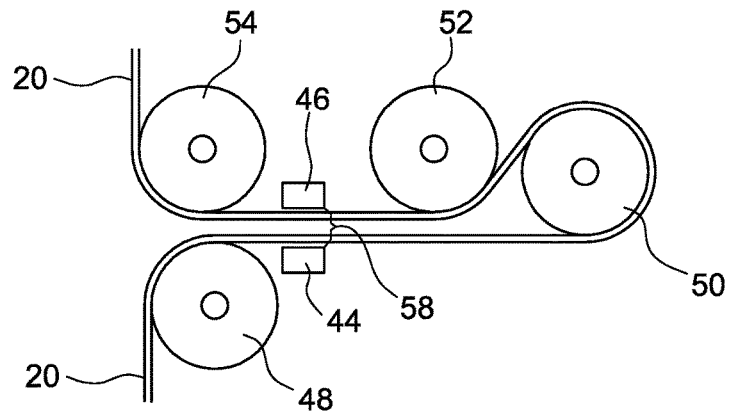

Preferably, as shown in FIGS. 6A-C, the axles for at least some rollers 52, 54 in the series of rollers are movable to facilitate stringing the web or film 20 into the C-Frame Scanner 40. As shown in FIG. 6A, the rollers 52, 54 are spaced apart from rollers 48, 50 in an open position to string up the web or film 20. Next, the rollers 52, 54 may be moved toward rollers 48, 50, such as in direction of arrows 53, 55 in FIG. 6B. In the closed position shown in FIG. 6C, the strung-up web or film 20 is shown in overlapping thickness in the measurement channel 58.

Figures 3, 4:
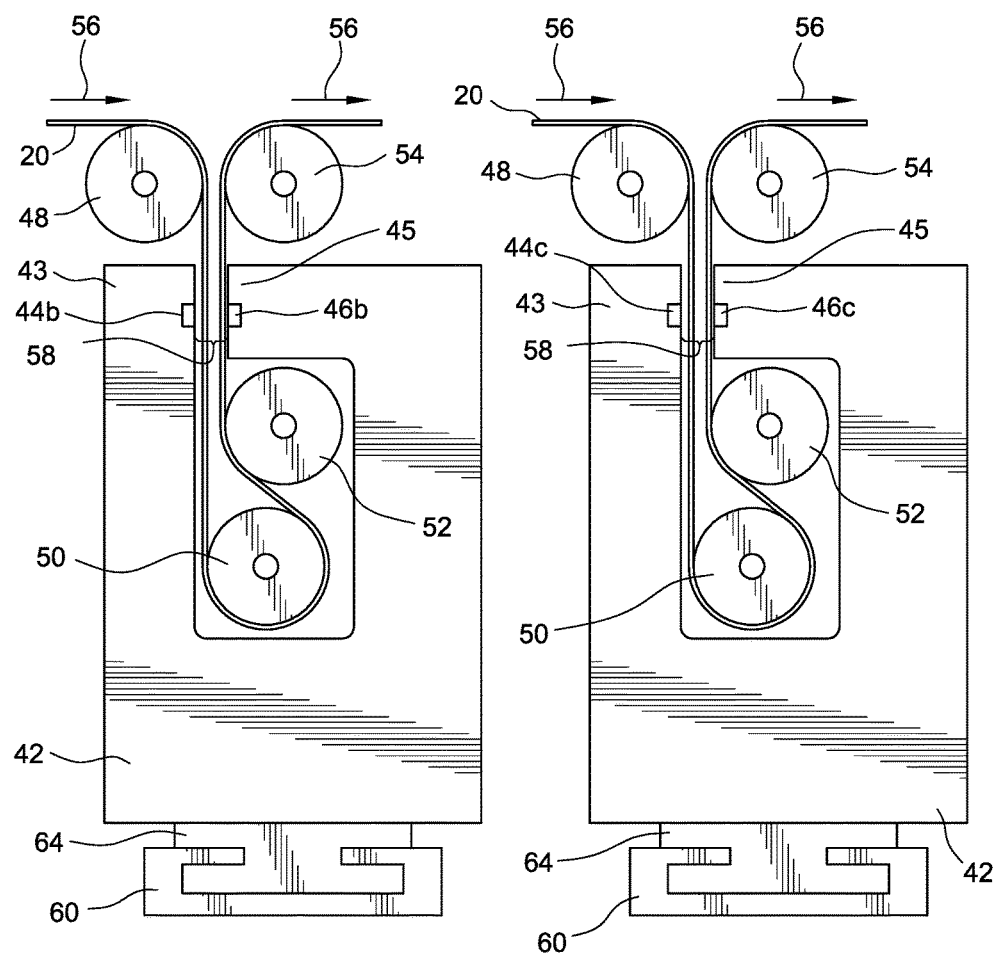
FIG. 3 is a schematic diagram of a cross-sectional view of a Double-Back Scanner with C-Frame Gauge according to a second embodiment of the invention.
FIG. 4 is a schematic diagram of a cross-sectional view of a Double-Back Scanner with C-Frame Gauge according to a third embodiment of the invention.

FIGS. 3 and 4 show variants of the C-Frame double-back scanner having alternative types of sensors on the arms of the C-Frame at the measurement channel 58. In FIG. 3, the first source 44b is an X-ray tube, and the first detector 46b is an X-ray detector. In FIG. 4, the first source 44c is a beta or gamma ray emitter and the first detector 46c is a beta or gamma ray detector. All other components of the C-Frame double back scanner 40 remain the same as with the embodiment shown in FIG. 2. Different measurement technologies may have varying sensitivities to registration issues between the two halves of the sensors. In this invention, the registration between the sensor halves 44, 46 is solely a function of the C-Frame integrity. This improvement opens the door to the possibility of sensors design which have highly demanding requirements with regard to distance and alignment stability. High precision, parallel plate capacitor designs fall into this category.

The measurement channel 58 preferably is established on the C-Frame Scanner with a small throat depth. This embodiment allows for higher performance. Unlike O-Frame sensor gauges such as shown in FIG. 1, the C-Frame Scanner 42 is not subject to shifts in sensor registration. A typical range of throat depth (e.g., measurement channel depth) that is effective for parallel plate capacitive sensors is from 5 cm to 50 cm owing to the ultra-high sensitivity to distance registration which is subject to greater degrees of degradation as throat depth widens. Other technologies may vary in this sensitivity and are purposefully designed to minimize the negative effects of mis-registration.

Figure 8:
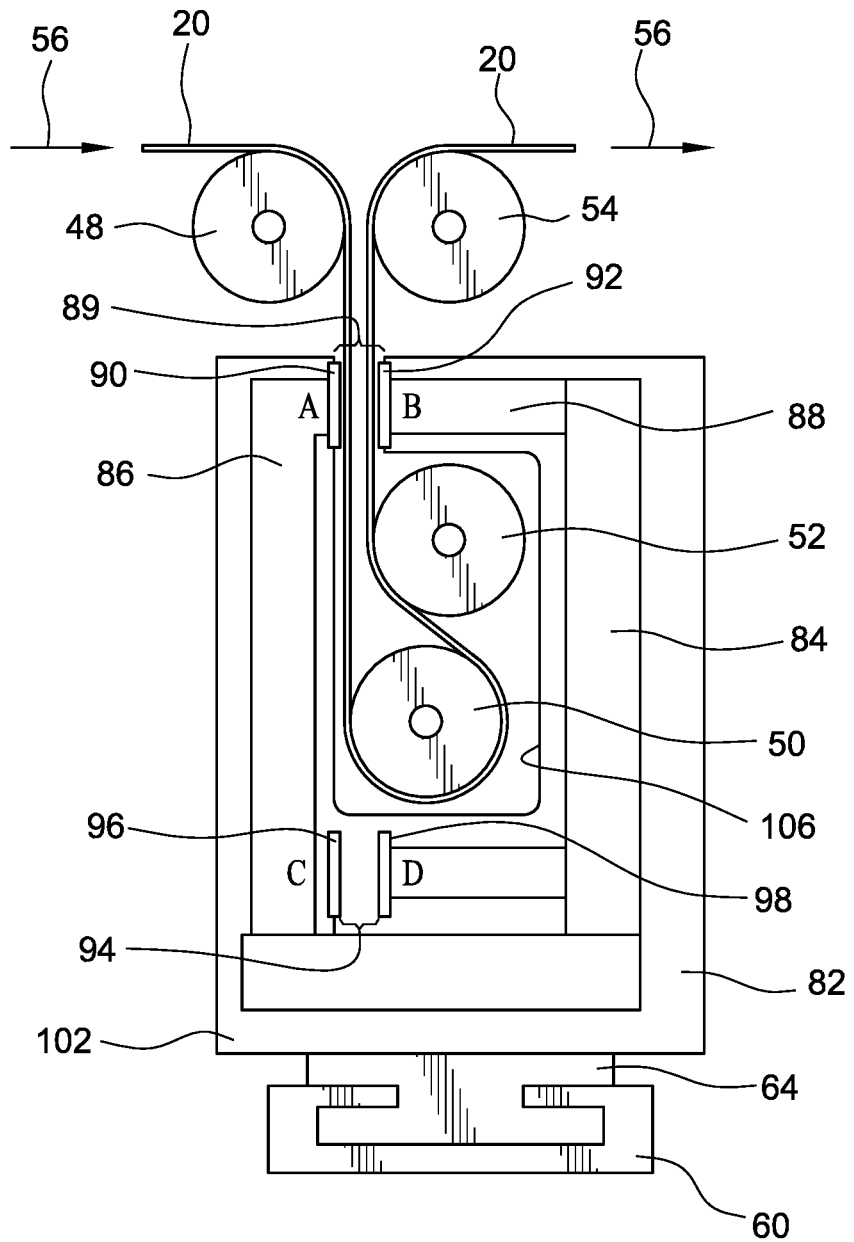
FIG. 8 is a schematic diagram illustrating a Double-Back Scanner with C-Frame Gauge with Capacitor Plates according to a fourth embodiment of the invention.

While many different non-contact sensor types may be used in conjunction with the frame 42 and in the measurement channel 58 thereof, one preferred sensor is a capacitive sensor with non-contact parallel plates, such as shown in FIGS. 8-10B. Referring first to FIGS. 8, 9A and 9B, the first plate 90 is associated with one side of the measurement channel 89 and the second plate 92 is associated with the opposite side of the measurement channel 89. The second plate 92 may have region(s) 93 of different capacitance for a multi-channel gauge design. In the embodiment shown in FIG. 8, the second plate 92 has one capacitive region 93. In the embodiment shown in FIG. 10A, the second plate 192 has three regions 193 B1, B2, B3 of different capacitance.

In the embodiment of FIG. 8, the C-Frame 84 additionally incorporates a reference channel 94, which spaces the capacitive sensor plates 96, 98 as same distance apart as the plates 90, 92 in the measurement channel 89. The second plate 98 in this embodiment has one capacitive region 199. The reference channel 94 serves dual purposes of (a) a comparative reference of distance registration, and (b) a comparative reference of the capacitance of free space to be used in differential measurements that compare the measurement parallel plates 90, 92 with the reference parallel plates 96, 98.

Figure 9A:
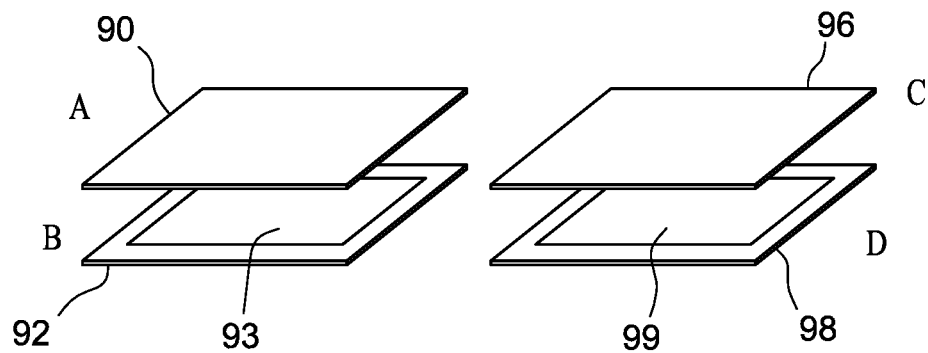
FIGS. 9A and 9B are schematic diagrams of a plate design and basic circuit for one configuration of the Double-Back Scanner with C-Frame Gauge with Capacitor Plates of FIG. 8.
Figure 9B:
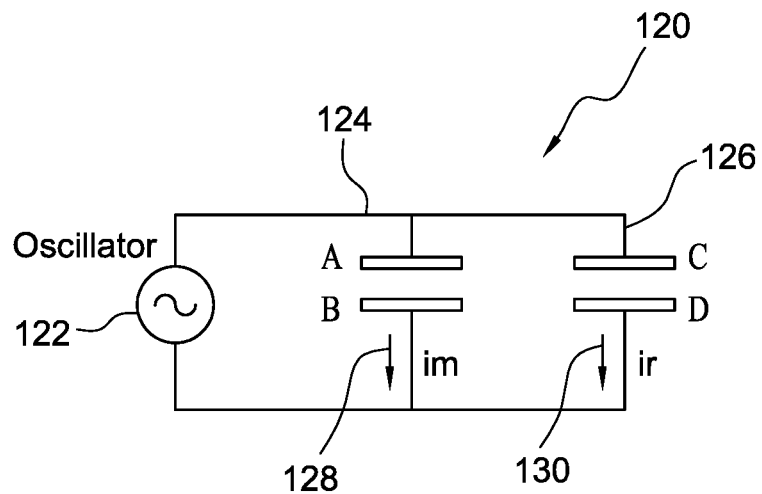

A basic circuit diagram shown in FIG. 9B shows the capacitor of plates in the measurement channel 89 in a circuit in parallel with the plates of the reference channel 94 and in parallel with an oscillator 122. A current 128 out of the measurement channel (im) and a current 126 out of the reference channel (ir) may be subtracted to provide a differential output signal. Using current to voltage conversions, a differential output voltage between the current of the measurement channel and the current of the reference channel may be calculated as Vout=Vim−Vir. Of special note is the fact that Vim=Vir in a balanced system when no materials are present in the measurement channel 89, theoretically yielding Vout=Vim−Vir=0. Optimum measurement performance can be obtained by trimming or compensating to yield this zero condition both before measurements begin or during process measurements by intermittently extracting the gauge to an off web position for trimming purposes. This can thus be used to compensate for any zero drift in measurements.

Figure 10A:
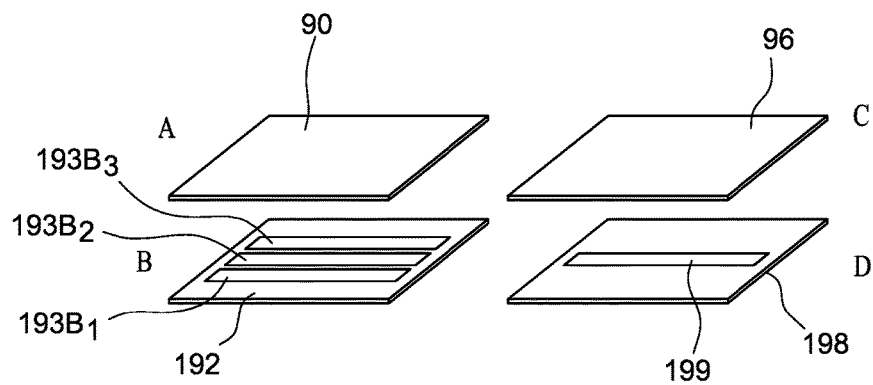
FIGS. 10A and 10B are schematic diagrams of a plate design and basic circuit for a second configuration of the Double-Back Scanner with C-Frame Gauge with Capacitor Plates of FIG. 8.
Figure 10B:
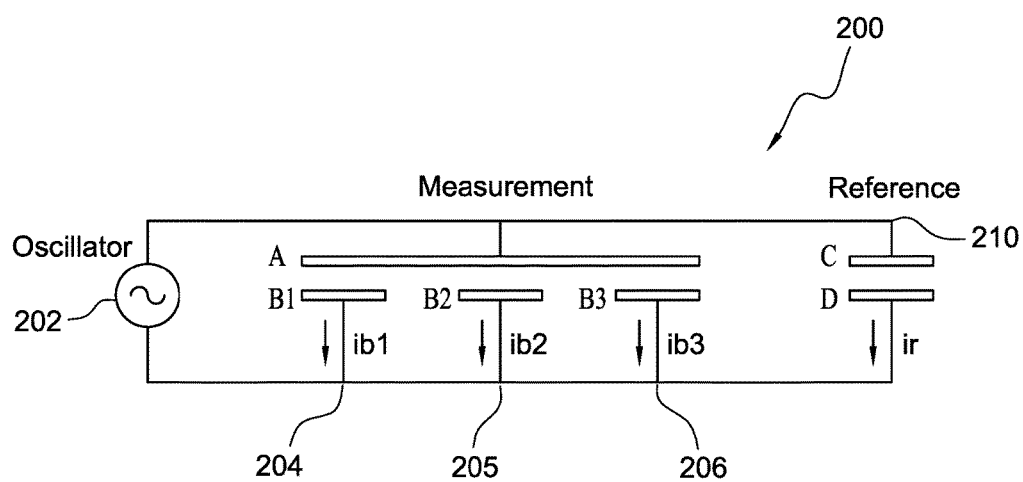

Turning next to the embodiment shown in FIGS. 10A and B, different capacitive plates are used in combination with the C-Frame 84 of FIG. 8. Here, the first capacitive plate 90 may be the same, but the second plate 192 includes regions of different capacitance 193 B1, B2, B3. And, in the reference channel 94, the capacitive plate 96 may be the same, but the second plate 198 may have a smaller capacitive region 199. A basic circuit diagram 200 for this alternative embodiment is set out in FIG. 10B. Here, the capacitor of plates in the measurement channel 89 again are in a circuit in parallel with the plates of the reference channel 94 and in parallel with an oscillator 202. Currents 204, 205, 206 out of the measurement channel (ib1, ib2, ib3) and a current 210 out of the reference channel (ir) may be compared to calibrate the double back scanner. Using current to voltage conversion, currents are converted to voltages for signal processing. The differential output voltages between the measurement channel and the reference channel may be calculated as Vout1=Vbi1−Vir; Vout2=Vb2−Vir; and Vout3=Vb3−Vir.

The C-Frame facilitates ultra-high registration of the upper and lower sensor bodies and may be used to measure thickness of a wide variety of geometries.

Embodiments of apparatus for measuring thickness or basis weight of a web or film according to the invention may be used to measure thickness of plastics, foils, papers, nonwovens and other web or film materials. In general, for polymeric films, the thicknesses are in the range of from 5 microns to 250 microns, and thickness measurement is desired to be within ±0.5%. Precision and accuracy of any measurement is assessed in non-scanning, fixed mode with specific testing of the impact, and then adding in the errors introduced by the scanning apparatus to meet an error budget.

An important advantage of the measurement apparatus and method according to the invention is that it provides a means to take advantage of relatively small "C" Frame Sensor constructions for use on wide web materials. "C" frame advantages include providing improved structural stability, leading to stable spacing and alignment, which directly relates to more stable and precise measurements. For some technologies, this may provide a marginal improvement which gives a superior performance. For other technologies, such as those having highly sensitive alignment and spacing requirements, the "C" frame affords the possible use on wide web processes.

As web material and layered composites continue to be made thinner and thinner, material parameters are increasingly more difficult to assess. The double layer of material provides improved precision and accuracy because more signal is present on a double layer of material rather than a single layer of material. Also, the double thickness of material in the prescribed presentation gives an inherent averaging effect in the machine direction. This is helpful for systems that are designed primarily for cross web monitoring and control. For these systems, averaging is typically done in the machine direction to improve cross web information.

Optionally, additional sensor pairs may be incorporated into the C-frame to supplement the primary sensor pair to yield multiple types of information or for compensation for the primary sensor pair measurement. This includes mounting adjunct sensors, such as an infrared thermometer for temperature data, a moisture sensor and a color sensor. All can be integral with or affixed to the C-frame structure.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

I claim:

1. An apparatus for measuring thickness or basis weight of a web or film, comprising:
    a frame having a first face spaced apart in opposing relation to a second face defining a measurement channel;
    a sensor comprising a first sensor component on or appended to the first face of the frame and a second sensor component on or appended to the second face of the frame; and
    a series of rollers adapted for contact with the web or film to guide the web or film into the measurement channel in an overlapping relation such that at least two portions of said web or film reside in said measurement channel for detection by the sensor.

2. The apparatus of claim 1, wherein the sensor comprises a non-contact displacement sensor selected from the group consisting of: parallel plate capacitive sensors, x-ray tube and detector sensors, beta source and beta detector sensors, gamma source and gamma detector sensors, and pulsed terahertz sources with sensors.

3. The apparatus of claim 1, wherein the series of rollers is configured so that more than two portions of said web reside in said measurement channel for detection by the sensor.

4. The apparatus of claim 1, further comprising: a linear slide to which the frame is secured, said linear slide adapted for cross-web movement to locate the frame along different locations across the web or film.

5. The apparatus of claim 1, further comprising: a linear slide to which the frame is secured, said linear slide adapted for movement to locate the sensor in position along the width of the web or film.

6. The apparatus of claim 5, wherein the linear slide is adapted for movement to locate the sensor to a position off of the web or film.

7. The apparatus of claim 1, wherein the frame further defines a reference channel spaced apart from the measurement channel, which reference channel registers a same or substantially same spaced apart distance as the measurement channel between the first face and second face of the frame.

8. The apparatus of claim 1, wherein the sensor comprises a parallel plate capacitive sensor and the first sensor component is a first plate and the second sensor component is a second plate.

9. The apparatus of claim 8, wherein the second sensor component is a second plate with multiple regions of different capacitance arranged in an array.

10. The apparatus of claim 8, further comprising a second sensor pair integral with or affixed to the frame.

11. The apparatus of claim 8, further comprising an adjunct sensor integral with or affixed to the frame.

12. A method for measuring thickness or basis weight of a web or film, comprising:
    threading the web or film over a series of rollers to guide the web or film into a measurement channel in an overlapping relation such that at least two portions of said web or film reside in said measurement channel; and
    detecting attenuation of a signal from a sensor source at one side of the measurement channel to a detector at an opposite side of the measurement channel.

13. The method of claim 12, wherein the sensor comprises a non-contact displacement sensor selected from the group consisting of: capacitive sensors, x-ray tube and detector sensors, beta source and beta detector sensors, gamma source and gamma detector sensors, and pulsed terahertz sources with sensors.

14. The method of claim 12, wherein the series of rollers is configured so that more than two portions of said web reside in said measurement channel for detection by the sensor.

15. The method of claim 12, further comprising: traversing the measurement channel by cross-web movement to locate the measurement channel along different locations across the web or film.

16. The method of claim 12, further comprising: traversing the measurement channel by cross-web movement to locate the measurement channel off of the web or film.

17. The method of claim 12, wherein the measurement channel is defined in a frame, and said frame further defines a reference channel spaced apart from the measurement channel, wherein gap spacing of the measurement channel is established with reference to gap spacing of the reference channel.

18. The method of claim 12, wherein the sensor comprises a parallel plate capacitive sensor having a first plate located at one side of the measurement channel and a second plate located at an opposite side of the measurement channel.

19. The method of claim 18, wherein the second plate has multiple regions of different capacitance arranged in an array.

* * * * *